United States Patent [19]

Fukaya et al.

[11] Patent Number: 5,208,339
[45] Date of Patent: May 4, 1993

[54] NITROGEN-CONTAINING PERFLUOROALKANOYL PEROXIDE AND METHOD FOR PRODUCTION THEREOF

[75] Inventors: Haruhiko Fukaya, Oobu; Takashi Abe, Kasugai; Eiji Hayashi, Konan; Yoshio Hayakawa, Aichiken, all of Japan

[73] Assignees: Agency of Industrial Science & Technology; Ministry of International Trade & Industry, Tokyo, Japan

[21] Appl. No.: 941,884

[22] Filed: Sep. 8, 1992

[30] Foreign Application Priority Data

Nov. 15, 1991 [JP] Japan .................................. 3-355487

[51] Int. Cl.$^5$ ............................................ C07D 265/30
[52] U.S. Cl. ........................................ 544/79; 544/66; 540/596
[58] Field of Search ...................... 544/79, 66; 540/596

[56] References Cited

PUBLICATIONS

Journal of Flourine Chemistry, vol. 22, 1983, pp. 541–556, Fuchikami, et al., "Direct Perfluoroalkylation of Functionalized Benzenes with Perfluoroalkyl Halides and Copper Bronze".

Journal of Organic Chemistry, vol. 47, 1982, pp. 2009–2013, Z. Chengxue, et al., "Thermal Decomposition of Some Perfluoro-and Polyfluorodiacyl Peroxides".

*Primary Examiner*—Marianne M. Cintins
*Assistant Examiner*—John Peabody
*Attorney, Agent, or Firm*—Oblon, Spivak, McClelland, Maier & Neustadt

[57] ABSTRACT

A nitrogen-containing perfluoroalkanoyl peroxide is provided which is represented by the formula:

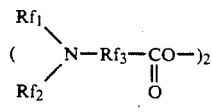

wherein $Rf_1$ and $Rf_2$ independently stand for an alkyl group of 1 to 5 carbon atoms, provided that $Rf_1$ and $Rf_2$ are joined to each other in one of the three patterns of union, 1) direct union, 2) union through the medium of an oxygen atom or 3) union through the medium of a nitrogen atom to form one of the three rings, i.e. five-membered ring, six-membered ring or seven-membered ring. The nitrogen-containing perfluoroalkanoyl peroxide is produced by a method which comprises oxidizing a compound represented by the following formula:

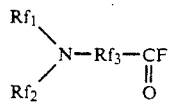

3 Claims, No Drawings

NITROGEN-CONTAINING PERFLUOROALKANOYL PEROXIDE AND METHOD FOR PRODUCTION THEREOF

BACKGROUND OF THE INVENTION

1. Field of the Invention

This invention relates to novel nitrogen-containing perfluoroalkanoyl peroxides and a method for the production thereof. More particularly, this invention relates to nitrogen-containing perfluoroalkanoyl peroxides suitable for use as a polymerization initiator for fluorine-containing monomers, as a reagent for introducing nitrogen-containing perfluoroalkyl groups, and as a raw material for perfluoro-tertiary diamines which are useful as heat transfer media or solvents and to a method for highly efficient production of the nitrogen-containing perfluoroalkanoyl peroxides from perfluoro(dialkylamino group-substituted carboxylic acid fluorides).

2. Prior Art Statement

It is known that perfluoroalkanoyl peroxides are useful as polymerization initiators for the production of fluorine-containing polymers (Japanese Patent Public Disclosure SHO 49(1974)-10290). It is also known that many perfluoroalkyl group-containing compounds exhibit useful qualities such as surface activity, lubricity, and physiological activity. As methods for producing perfluoroalkyl group-containing compounds, those using perfluoroalkyl iodides ["Journal of Fluorine Chemistry", Vol. 22, page 541, (1983)] and FITS reagents ["Journal of Synthetic Organic Chemistry, Japan", Vol. 41, page 251 (1983)] and those by perfluoroalkylation using fluorine-containing alkanoyl peroxides ["Journal of Synthetic Organic Chemistry, Japan", Vol. 46, page 1205 (1988)] have been proposed to date.

However, the only perfluoroalkanoyl peroxides available up to now have been: (1) perfluoroalkanoyl peroxides produced from a perfluorocarboxylic acid chloride as a raw material and (2) perfluoroalkanoyl peroxides produced from a perfluorocarboxylic acid fluoride containing an oxygen atom in the perfluoroalkyl group thereof by oligomerizing reaction of hexafluoropropene oxide, this latter group of perfluoroalkanoyl peroxides consisting of (a) bis(perfluoro-2-methyl-3-oxahexanoyl) peroxides [referred to in the Journal of Organic Chemistry, Vol. 47, page 2009 (1982)] and (b) bis perfluoro-2,5-dimethyl-3,6-dioxanonanoyl) peroxide, bis(perfluoro-2,5,8-trimethyl-3,6,9-trioxadecanoyl) peroxide and bis(perfluoro-2,5,8,11,14-pentamethyl-3,6,9,12,15-pentaoxaoctadecanoyl) peroxides [all three of which are referred to in the proceeding of the 15th Symposium on Flourine Chemistry, 0-29 held on Oct. 22 and 23, 1990 in Tokyo]. In the circumstances, a need has arisen for perfluoroalkanoyl peroxides suitable for use in various industrial applications.

SUMMARY OF THE INVENTION

This invention was accomplished in response to this need and has as its object to provide novel nitrogen-containing perfluoroalkanoyl peroxides which are useful in a wide range of applications requiring, for example, a polymerization initiator for fluorine-containing monomers or a reagent for the introduction of nitrogen-containing perfluoroalkyl groups into compounds, and also as a heat transfer medium and a solvent.

The inventors conducted a study for achieving this object. As a result, they have found that novel nitrogen-containing perfluoroalkanoyl peroxides are obtained in a relatively high yield by using as a raw material a nitrogen-containing perfluorocarboxylic acid fluoride and oxidizing this raw material to form a peroxide bond therein and that these nitrogen-containing perfluoroalkanoyl peroxides can be utilized in the same applications as the conventional perfluoroalkanoyl peroxides. This invention has been completed on the basis of this finding.

To be specific, this invention relates to a nitrogen-containing perfluoroalkanoyl peroxide represented by the formula (I):

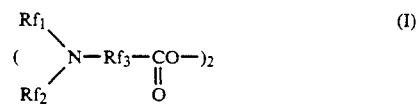

wherein $Rf_1$ and $Rf_2$ independently stand for a perfluoroalkyl group of 1 to 5 carbon atoms, provided that $Rf_1$ and $Rf_2$ are joined to each other in one of the three patterns, 1) direct union, 2) union through the medium of an oxygen atom or 3) union through the medium of a nitrogen atom, to form one of three rings, i.e. five-membered ring, six-membered ring or seven-membered ring, and $Rf_3$ stand for a perfluoroalkyl group of 1 to 3 carbon atoms.

The nitrogen-containing perfluoroalkanoyl peroxide of this invention is provided by a method which comprises oxidizing a perfluoro(dialkylamino group-substituted carboxylic acid fluoride) represented by the formula (II):

wherein $Rf_1$, $Rf_2$, and $Rf_3$ have the same meanings as defined above.

DESCRIPTION OF THE PREFERRED EMBODIMENTS

The nitrogen-containing perfluoroalkanoyl peroxides of this invention which are represented by the aforementioned general formula are novel compounds which have not been reported in the literature. Concrete examples of the perfluorodialkylamino group,

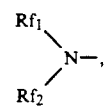

in the general formula are shown below.

In the following formulas, each of n and m stands for an integer in the range between 1 and 5.

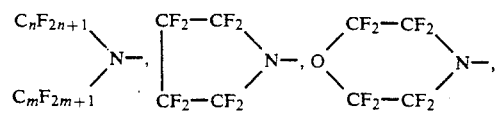

-continued

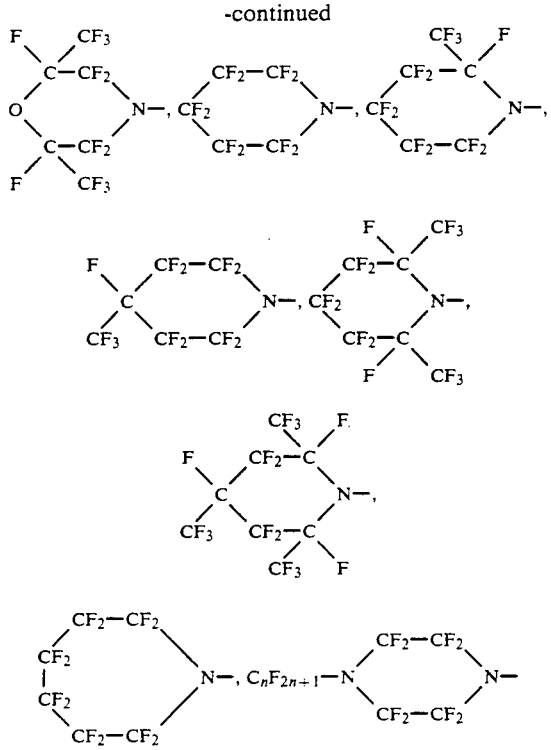

Concrete examples of Rf₃ are shown below.

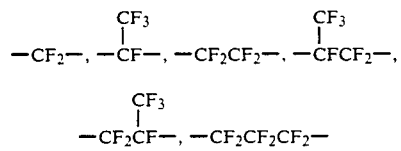

The nitrogen-containing perfluoroalkanoyl peroxide of this invention which is represented by the general formula (I) is produced by the method of this invention described below. As the raw material, a perfluoro(dialkylamino group-substituted carboxylic acid fluoride) represented by the general formula (II) is used. This is easily produced by subjecting an ester or a halogenide of a corresponding dialkylamino group-substituted carboxylic acid to electrolytic fluorination in hydrogen fluoride.

The nitrogen-containing perfluoroalkanoyl peroxide which is represented by the formula (I) is produced by oxidizing the perfluoro(dialkylamino group-substituted carboxylic acid fluoride). Two methods are available for effecting the oxidation. In the first method the oxidation is effected with hydrogen peroxide in the presence of at least one alkali selected from among sodium hydroxide, potassium hydroxide, sodium carbonate, potassium carbonate, sodium hydrogen carbonate, and potassium hydrogen carbonate and in the second method it is effected by the use of at least one alkali metal peroxide or alkaline earth metal peroxide selected from among potassium peroxide, sodium peroxide, lithium peroxide and barium peroxide.

In the first method, the molar ratio of an acid fluoride, hydrogen peroxide, and an alkaline metal salt to be used for the reaction is generally in the range of 1:0.3–20:0.3–10, preferably 1:0.5–10:0.5–7. In the second method, the molar ratio of an acid fluoride and an alkali metal peroxide or alkaline earth metal peroxide is generally in the range of 1:0.3–20, preferably 1:0.5–15. The yield in which the nitrogen-containing perfluoroalkanoyl peroxide aimed at is produced is unduly low if the molar ratio of hydrogen peroxide or that of the alkali metal salt used in the first method or the molar ratio of the alkali metal peroxide or that of the alkaline earth metal peroxide used in the second method relative to the acid fluoride as the raw material is unduly high. If this molar ratio is unduly low, the reaction time is elongated and the yield of the nitrogen-containing perfluoroalkanoyl peroxide is also lowered. The reaction temperature and the reaction time are generally selected in the ranges between −20° C. and +40° C. and between 0.5 and 8 hours. Since these reaction conditions are variable with the kinds of raw material and reagent for reaction, the molar ratio of the raw material to the reagent for reaction, and the method for synthesis of the peroxide bond, they are desired to be suitably selected in consideration of the yield of the product aimed at.

In the method of this invention, the reaction is preferably carried out in a fluorinated hydrocarbon type solvent such as 1,1,2-trichloro-1,2,2-trifluoroethane or perfluorooctane because this enables the produced nitrogen-containing perfluoroalkanoyl peroxide to be handled safely and also enables the peroxide to be handled easily in the synthesis reaction in which it is used.

The nitrogen-containing perfluoroalkanoyl peroxide produced as described above are novel compounds which have not been reported in the literature. The nitrogen-containing perfluorodialkyl chain of these compounds exhibits strong hydrophobicity and lipophobicity. The nitrogen-containing perfluoroalkanoyl peroxides are therefore useful as polymerization initiators for such electron attractive monomers as tetrafluoroethylene, vinyl chloride and hexafluoropropane. They can also be used advantageously as fluoroalkylating agents of electron excessive aromatic compounds such as benzene and pyrrole necessary for the production of useful compounds which take advantage of the characteristic properties of the nitrogen-containing perfluoroalkyl group.

They can also advantageously by used as a polymerization initiator for fluorine-containing monomers as a reagent for introduction of a nitrogen-containing perfluoroalkyl group in compounds, and as a raw material for perfluoro-tertiary diamines which are useful as heat transfer media or solvents.

This invention will now be described more specifically below with reference to working examples. It should be noted, however, that this invention is not limited in any sense by these examples.

EXAMPLE 1

First, perfluoro(3-morpholinopropionic acid fluoride) was synthesized by subjecting methyl 3-morpholinopropionate to electrolytic fluorination and then purified by distillation.

In a three-neck flask, 50 ml of 1,1,2-trichloro-2,2,1-trifluoroethane ($CF_2ClCClF_2$) and 10 ml of an aqueo 3M sodium hydroxide solution (containing about 15 mmols of NaOH) and 2 ml of an aqueous 30 wt % hydrogen peroxide solution (containing about 20 mmols of $H_2O_2$) added thereto were cooled to −15° C. To the resultant cooled mixture, 15.0 mmols of perfluoro(3-morpholinopropionic acid fluoride) 60.0% in purity was added piecemeal under stirring. The reaction mixture consequently obtained was further stirred at 0° C. for 25 minutes to complete the reaction. After the reaction was completed, the produced solution was washed three times with a saturated aqueous solution of sodium hydrogen carbonate, further washed several times with ice water, and dried with anhydrous sodium sulfate.

The amount of the produced peroxide was found by iodometric analysis to be 4.2 mmols and the yield thereof to be 56% (mol yield based on perfluoro acid fluoride). By chemical analysis, the produced compound was identified to be bis(perfluoro-3-morpholinopropionyl) peroxide having a 10-hour half period temperature of 24.1° C. and an active oxygen content of 2.1%.

The bis(perfluoro-3-morpholinopropionyl) peroxide was a novel peroxide which was colorless and transparent in $CF_2ClCFCL_2$ and was stable at low temperatures (at $-20°$ C.) for more than one month.

The $^{19}$F-NMR data (chemical shift; $^{19}$F-NMR based on $CFCl_3$ in a $CDCl_3$ solvent) of this compound are shown below.

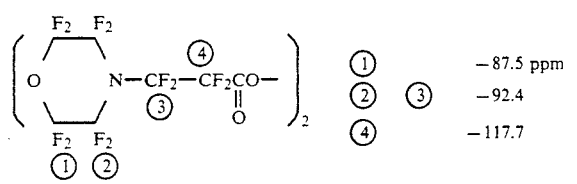

The kinetic constants of thermal decomposition at varying temperatures and the activation energy in $CF_2ClCFCl_2$ are shown in Table 1.

TABLE 1

| Temperature (°C.) | $k \times 10^5 \,(s^{-1})$ | Activation energy (kcal/mol) |
|---|---|---|
| 30 | 3.82 ± 0.05 | |
| 35 | 10.6 ± 0.05 | |
| 40 | 16.3 ± 0.05 | 25.7 ± 1.2 |
| 44 | 25.9 ± 0.05 | |

The identify of this compound was confirmed by the reaction of the following Referential Example 1.

REFERENTIAL EXAMPLE 1

When 69.9 g of a $CF_2ClCFCl_2$ solution containing 4.20 mmols of the bis(perfluoro-3-morpholinopropionyl) peroxide obtained in Example 1 was heated and refluxed overnight, then distilled in a rotary evaporator to expel the solvent and purified by the process of sublimation, 1.42 g of a white solid substance was obtained which exhibited a melting point of 51.0°–52.5° C. and a boiling point of 190.0°–191.0° C. This substance, on analysis by $^{19}$F-NMR, IR, and MS, was identified to be perfluoro(1,4-dimorpholinobutane) (yield 51%) obtained in the form of a coupling product via the process of decomposition of the peroxide mentioned above.

EXAMPLE 2

The procedure of Example 1 was faithfully repeated, except that perfluoro(3-dimethylaminopropionic acid fluoride) was used in the place of the perfluoro(3-morpholinopropionic acid fluoride). The perfluoro(3-dimethylaminopropionic acid fluoride) (purity 81.7% and content 30.4 mmols) was synthesized by subjecting methyl 3-dimethylamino-propionate to electrolytic fluorination and then purified before use.

The compound, consequently obtained when analyzed in the same manner as in Example 1, was found to be bis(perfluoro-3-dimethylaminopropionyl) peroxide having a 10-hour half period temperature of 21.3° C. and an active oxygen content of 2.7%. The amount of this compound produced was found to be 12.2 mmols and the yield thereof to be 80%.

The $^{19}$F-NMR data of this compound are shown below.

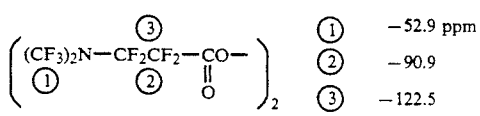

The kinetic constants of thermal decomposition at different temperatures and the activation energy in $CF_2ClCFCl_2$ are shown in Table 2.

TABLE 2

| Temperature (°C.) | $k \times 10^5 \,(s^{-1})$ | Activation energy (kcal/mol) |
|---|---|---|
| 30 | 5.36 ± 0.14 | |
| 35 | 9.33 ± 0.06 | |
| 40 | 17.2 ± 0.02 | 20.7 ± 0.2 |
| 48 | 34.4 ± 0.61 | |

EXAMPLE 3

The procedure of Example 1 was faithfully repeated, except that perfluoro(3-pyrrolidinopropionic acid fluoride) was used in the place of the perfluoro(3-morpholinopropionic acid fluoride). The perfluoro(3-pyrrolidinopropionic acid fluoride) (purity 81.6% and content 16.2 mmols) was synthesized by subjecting methyl 3-pyrrolidinopropionate to electrolytic fluorination and was purified before use.

The compound consequently obtained, when analyzed in the same manner as in Example 1, was identified to be bis(perfluoro-3-pyrrolidinopropionyl) peroxide having a kinetic constant, k, of $6.15 \times 10^{-4} \,(s^{-1})$ at 48° C. and an active oxygen content of 2.2%. The amount of the product was found to be 5.42 mmols and the yield thereof to be 67%.

The identity of this compound was confirmed by the reaction shown in the following Referential Example 2.

REFERENTIAL EXAMPLE 2

When 59.9 g of a $CF_2ClCFCl_2$ solution containing 2.64 mmols of the peroxide obtained in the Example 3 was refluxed overnight, distilled to expel the solvent in the same manner as in Referential Example 1, and then purified with GC, 1.06 g of a colorless transparent solution was obtained which exhibited a melting point of 29.5°–31.0° C. and a boiling point of 187.5°–188.5° C. The solution, on analysis by $^{19}$F-NMR, IR, and MS, was identified to be a perfluoro(1,4-dipyrrolidinobutane) (yield 64%) obtained in the form of a coupling product through the process of decomposition of the peroxide.

EXAMPLE 4

The procedure of Example 1 was faithfully repeated, except that perfluoro(3-piperidinopropionic acid fluoride) was used in the place of the perfluoro(3-morpholinopropionic acid fluoride). The perfluoro(3-piperidinopropionic acid fluoride) (purity 81.7% and content 34.2 mmols) was synthesized by subjecting methyl 3-piperidinopropionate to electrolytic fluorination and purified before use.

The compound, when analyzed in the same manner as in Example 1, was found to be bis(perfluoro-3-piperidinopropionyl) peroxide having a 10-hour half period temperature of 22.2° C. and an active oxygen content of 2.0%. The amount of this compound produced was found to be 34.2 mmols and the yield thereof to be 60%.

The kinetic constants of thermal decomposition at different temperatures and the activation energy in $CF_2ClCFCl_2$ are shown in Table 3.

TABLE 3

| Temperature (°C.) | $k \times 10^5 (s^{-1})$ | Activation energy (kcal/mol) |
|---|---|---|
| 30 | 5.69 ± 0.07 | |
| 35 | 6.91 ± 0.17 | 23.4 ± 0.2 |
| 40 | 15.9 ± 0.19 | |
| 48 | 25.4 ± 0.49 | |

EXAMPLE 5

The procedure of Example 1 was faithfully repeated, except that perfluoro(morpholinoacetyl fluoride) was used in place of the perfluoro(3-morpholinopropionic acid fluoride). The perfluoro(morpholinoacetyl fluoride) (purity 91.8% and content 15.1 mmols) was synthesized by subjecting methyl morpholinoacetic acid to electrolytic fluorination and purified before use.

The compound consequently obtained, when analyzed in the same manner as in Example 1, was identified to be bis(perfluoro-morpholinoacetyl) peroxide having an active oxygen content of 2.5%. The amount of the product was found to be 3.6 mmols and the yield thereof to be 48%.

EXAMPLE 6

The procedure of Example 1 was faithfully repeated, except that perfluoro(3-dimethylaminoisobutyric acid fluoride) was used in place of the perfluoro(3-morpholinopropionic acid fluoride). The perfluoro(3-dimethylaminoisobutyric acid fluoride) (purity 79.7% and content 15.3 mmols) was synthesized by subjecting methyl 3-dimethylaminoisobutyrate to electrolytic fluorination and purified before use.

The compound consequently obtained, when analyzed in the same manner as in Example 1, was identified to be bis(perfluoro-3-dimethylaminoisobutyryl) peroxide having an active oxygen content of 2.3%. The amount of the compound obtained was found to be 3.6 mmols and the yield thereof to be 48%.

What is claimed is:

1. A nitrogen-containing perfluoroalkanoyl peroxide represented by the formula:

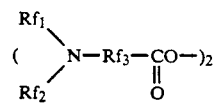

wherein $Rf_1$ and $Rf_2$ independently stand for a perfluoroalkyl group of 1 to 5 carbon atoms, joined to each other through an oxygen atom to form a five-membered ring, six-membered ring or seven-membered ring, and $Rf_3$ stands for a perfluoroalkylene group of 1 to 3 carbon atoms.

2. A nitrogen-containing perfluoroalkanoyl peroxide according to claim 1, wherein the group

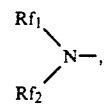

is selected from the group consisting of

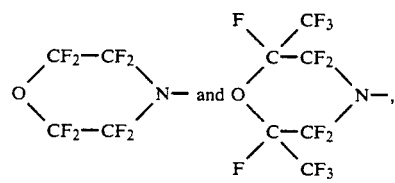

wherein n and m each stand for an integer in the range between 1 and 5.

3. A nitrogen-containing perfluoroalkanoyl peroxide according to claim 1, wherein the perfluoroalkylene group is selected from the group consisting of

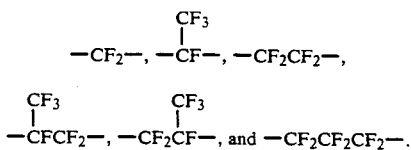

* * * * *